(12) United States Patent
Papirov et al.

(10) Patent No.: US 9,498,236 B2
(45) Date of Patent: Nov. 22, 2016

(54) HIGH PRESSURE BALLISTIC EXTRACORPOREAL SHOCKWAVE DEVICE, SYSTEM AND METHOD OF USE

(71) Applicant: HI IMPACTS LTD, Kiryat Ono (IL)

(72) Inventors: Eduard Papirov, Hod HaSharon (IL); Itzhak Friedman, Kiryat Ono (IL)

(73) Assignee: HI IMPACTS LTD, Kiryat Ono (IL)

( * ) Notice: Subject to any disclaimer, the term of this patent is extended or adjusted under 35 U.S.C. 154(b) by 0 days.

(21) Appl. No.: 14/375,952

(22) PCT Filed: Jan. 31, 2013

(86) PCT No.: PCT/IL2013/050086
§ 371 (c)(1),
(2) Date: Jul. 31, 2014

(87) PCT Pub. No.: WO2013/114366
PCT Pub. Date: Aug. 8, 2013

(65) Prior Publication Data
US 2014/0350438 A1    Nov. 27, 2014

Related U.S. Application Data

(60) Provisional application No. 61/592,617, filed on Jan. 31, 2012.

(51) Int. Cl.
*A61H 1/00* (2006.01)
*A61B 17/22* (2006.01)
*A61B 17/225* (2006.01)
*A61N 7/00* (2006.01)
*A61B 17/00* (2006.01)

(52) U.S. Cl.
CPC ....... *A61B 17/22004* (2013.01); *A61B 17/225* (2013.01); *A61N 7/00* (2013.01); *A61B 2017/00544* (2013.01); *A61B 2017/22027* (2013.01)

(58) Field of Classification Search
CPC ........................... A61N 7/00; A61H 23/0245
See application file for complete search history.

(56) References Cited

U.S. PATENT DOCUMENTS

| | | | | |
|---|---|---|---|---|
| 5,160,336 | A * | 11/1992 | Favre | A61B 17/22004 601/108 |
| 6,264,660 | B1 * | 7/2001 | Schmidt | A61B 17/8847 606/100 |
| 7,470,274 | B2 | 12/2008 | Lebet | |
| 7,485,101 | B1 * | 2/2009 | Faragalla | A61B 17/22004 600/437 |
| 2007/0025510 | A1 | 2/2007 | Buchholtz et al. | |
| 2010/0198114 | A1 | 8/2010 | Novak et al. | |
| 2010/0256535 | A1 | 10/2010 | Novak et al. | |
| 2011/0275965 | A1 | 11/2011 | Donnet et al. | |
| 2011/0295160 | A1 | 12/2011 | Hart | |

* cited by examiner

*Primary Examiner* — Tse Chen
*Assistant Examiner* — Hien Nguyen
(74) *Attorney, Agent, or Firm* — The Law Office of Joseph L. Felber

(57) ABSTRACT

The present invention relates to a device, system and a method for extracorporeal Shockwave treatment and in particular, to such a device, system and method in which a Shockwave is produced by a high pressure ballistic device utilizing a regulated high pressure energy source for generating an initial ballistic collision producing an initial Shockwave and an electromagnetic solenoid as reloading apparatus facilitating the formation of subsequent and/or successive Shockwaves.

21 Claims, 11 Drawing Sheets

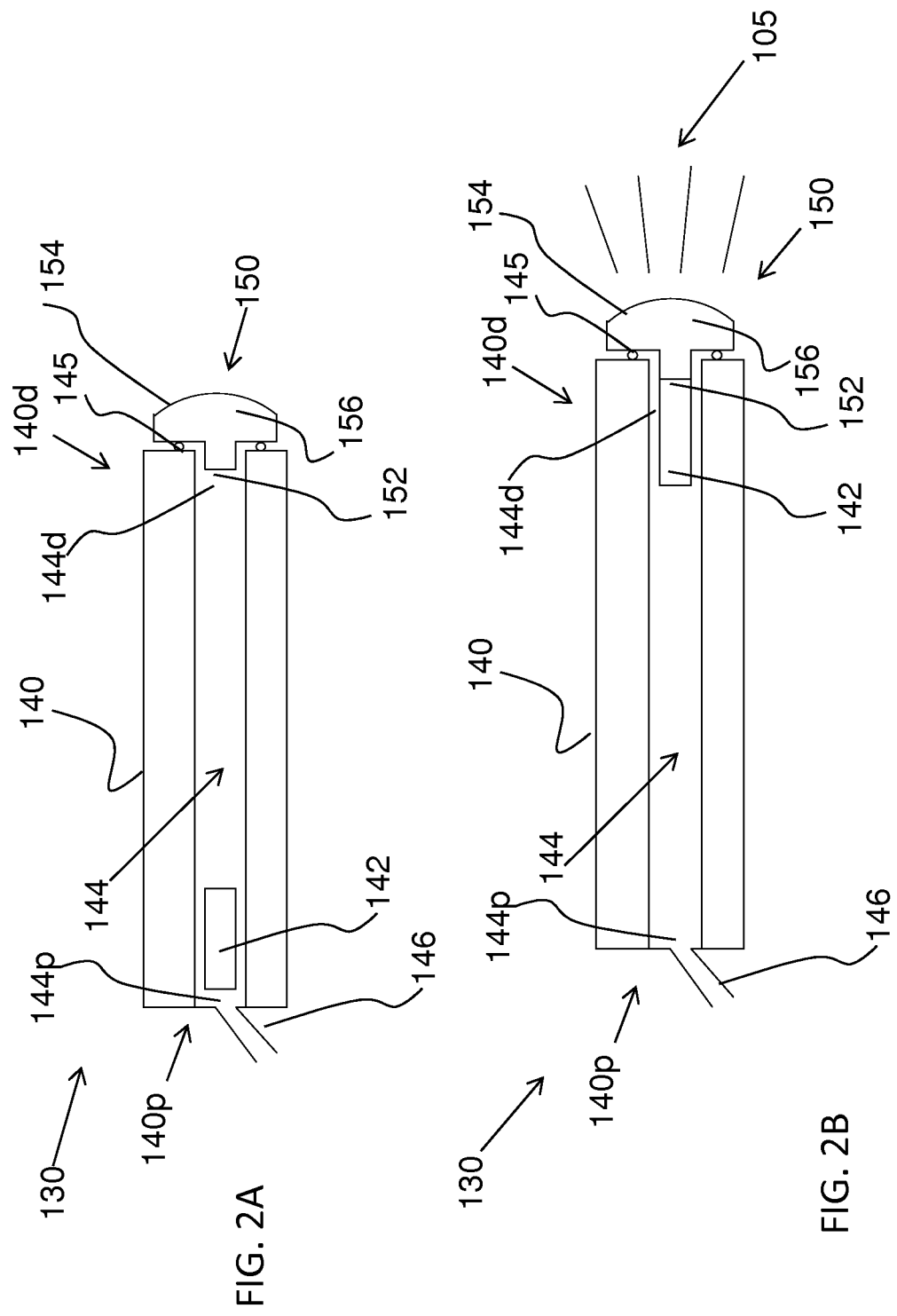

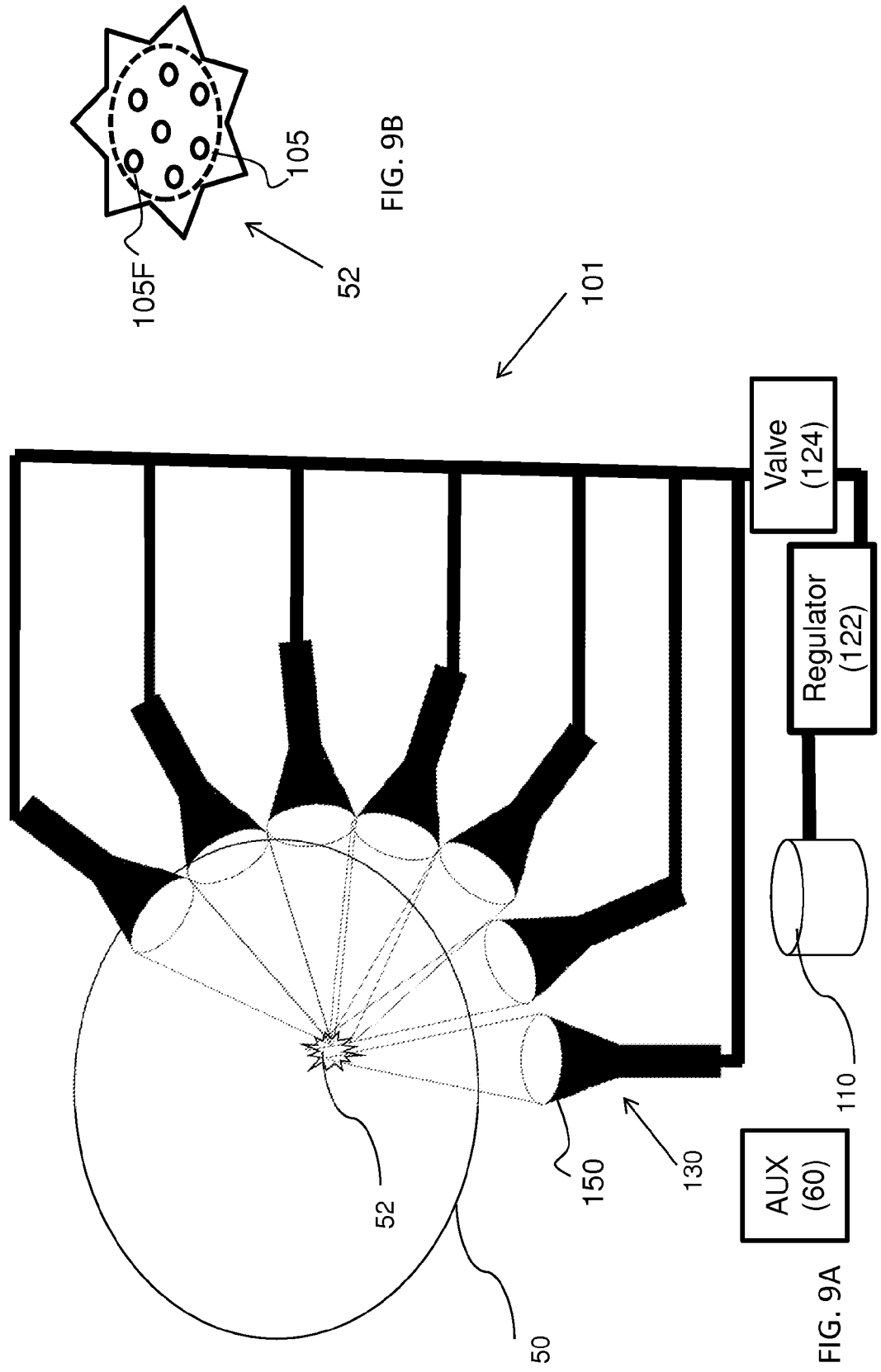

HIGH PRESSURE BALLISTIC EXTRACORPOREAL SHOCKWAVE DEVICE, SYSTEM AND METHOD OF USE

This Application is a national phase of, and claims priority from, PCT Application No. PCT/IL2013/050086, filed on Jan. 31, 2013, which claims priority from U.S. Provisional Application No. 61/592,617, filed Jan. 31, 2012, which is hereby incorporated by reference as if fully set forth herein.

FIELD OF THE INVENTION

The present invention relates to an extracorporeal shockwave treatment device, system and method and in particular, to such a device, system and method in which a shockwave is produced by a high pressure ballistic device.

BACKGROUND OF THE INVENTION

Extracorporeal shockwave therapy (herein referred to as 'ESWT') is non-surgical, non-invasive treatment of medical conditions using acoustic shockwaves. First use of shockwave therapy in the early 1980's was utilized to fragment kidney stones termed shockwave lithotripsy. Continued development of shockwave treatment showed the possibility of stimulating bone formation, angiogenesis, chronic orthopedic inflammation healing, bone healing (osteogenesis), wound healing, revascularization, angiogenesis are well known and described in medical literature.

A shockwave is a form of acoustic energy resulting from phenomena that create a sudden intense change in pressure for example an explosion or lightning. The intense changes in pressure produce strong waves of energy that can travel through any elastic medium such as air, water, human soft tissue, or certain solid substances such as bone.

Acoustic shockwaves may be generated by various methods, electrohydraulic (also referred to as spark gap), electromagnetic (also referred to as 'EMSE'), piezoelectric and ballistic shockwave.

Each method needs an apparatus to focus the generated shockwave so as to provide a focal point and/or focal zone for the treatment area. In the focal zone shockwaves produce much higher pressure impulses as compared with the zones outside of the focal zone.

Mechanical means for focusing each of these methods is generally realized with an appropriate arrangement of surfaces reflecting the wave toward the desired focal point and/or an appropriate arrangement of the generating devices.

Spark gap systems incorporate an electrode (spark plug), to initiate a shockwave, and ellipsoid to focus the shockwave. EMSE systems utilize an electromagnetic coil and an opposing metal membrane. Piezoelectric systems form acoustical waves by mounting piezoelectric crystals to a spherical surface to provide focus. Of the three systems, the spark gap system is generally preferred in the art for generating therapeutic shockwaves ESWT as it introduces more of the generated shockwave energy to the treatment target site.

In spark gap systems, high energy shockwaves are generated when electricity is applied to an electrode positioned in an ellipsoid immersed in treated water. When the electrical charge is fired, a small amount of water is vaporized at the tip of the electrode and a shockwave is produced. The shockwave ricochets from the side of an ellipsoid and converges at a focal point, which may then be transferred to the area to be treated.

In electromagnetic systems an electrical impulse is circulated in a coil. The coil produces an electromagnetic field that expels a metallic membrane to produce the mechanical impulse.

In piezoelectric systems ceramic material with piezoelectric characteristics is subjected to an electrical impulse. The electric impulse modifies the dimension of the ceramic material to generate the desired mechanical impulse. A focal point is attained by covering a concave spherical surface with piezoelectric ceramics converging at the center of the sphere.

The electrohydraulic, electromagnetic, and piezoelectric are all forms of shockwave generators that utilize high voltage power sources from 10 kV to about 25 kV in order to generate the required shockwave of about 100 bar to about 1000 bar). The drawbacks for such high voltage shockwave technology includes limitations both relating to the actual treatment and to the actual device and system. Treatment related limitations for example include production of a limited focal zone treatment area and low treatment efficacy. System limitations for example include cost, size, and durability where systems are generally expensive, large, heavy and require frequent maintenance. However, the biggest limitation of such system relates to the operating costs where such systems require many disposable accessories and integral electronic parts.

While high voltage device produce a shockwave pressure wave of about 100 bar to about 1000 bar, state of the art ballistic shockwave system offer generation of low level shockwaves, having pressure wave from about 50 bar to about 150 bar. As its name suggests ballistic shockwave system generate shockwaves as a result of a ballistic collision between a projectile and a generating surface. The projectile is accelerated and allowed to collide with the shockwave generating surface.

State of the art, ballistic shockwave systems are utilized for medical applications such as in physiotherapy applications for example for the treatment of inflammations and/or in dermatology and cosmetic applications, for example in the treatment of cellulite.

Current ballistic shockwave systems are limited in that a low pressure gas source (1-6 bar) leads to shockwaves that have low tissue penetration, small treatment and/or focal zone, high rates of re-treatment, discomfort due to the applicator's movement during the ballistic collision, are not readily mobile as they require an air compressor to produce the appropriate pressure. Other prior art ballistic shockwave system utilize an operational pressure of 15-30 bar, for example as described in U.S. Pat. No. 7,470,274 to Lebet. Moreover ballistic shockwave system generally do not provide for non-invasive extracorporeal shockwave treatment.

Similarly other prior art US2005/0209586, U.S. Pat. No. 6,413,230, WO2003084608, WO2008/007502 A1, WO2008/145273, U.S. Pat. No. 6,736,784, WO2010049519 describe ballistic shockwave systems using low level shock wave production by low gas pressure ballistic technology.

Other forms of ballistic shockwave generators include electromagnetic ballistic systems are further limited in that they tend to heat up and therefore require a cooling system due to the inclusion of an electromagnetic components.

SUMMARY OF THE INVENTION

There is an unmet need for, and it would be highly useful to have, a device, system and a method for a high pressure ballistic shockwave device for producing extracorporeal shockwaves for various non-invasive extracorporeal treatment and/or topical treatment, where optionally and preferably the operational pressure is from about 50 bar to about 100 bar.

A preferred embodiment of the present invention provides a system for producing extracorporeal ballistic shockwaves, the system comprising: at least one high pressure ballistic shockwave applicator, comprising a projectile accelerating portion and at least one shockwave generating portion; the shockwave is generated by a collision between an accelerated projectile disposed within the projectile accelerating portion against a shockwave generating surface disposed in the shockwave generating portion; a high pressure fluid source and a high pressure flow controller to energize and accelerate the projectile in a controllable and directed manner; the system characterized in that the high pressure fluid source is controlled with the flow controller such that the operational pressure utilized to accelerate the projectile is at least about 50 bar and up to about 100 bar.

Optionally high pressure fluid source has a fluid pressure up to about 300 bar.

Optionally the accelerating portion may further comprises a solenoid based projectile reloading apparatus.

Optionally the high pressure fluid source is selected from the group consisting of internal gas cylinder, external gas cylinder, gas pressure pump, gas pressure reservoir, compressor, pneumatic pump, any combination thereof.

Optionally the fluid providing the high pressure fluid source is nitrogen, air or Carbon dioxide ($CO_2$).

Optionally the system may utilize a plurality of high pressure ballistic shockwave applicators.

Optionally the system may utilize a plurality of shockwave generating portions. Optionally the plurality of shockwave generating portions may be arranged relative to one another to form a shockwave treatment focal zone.

Optionally a shockwave focal surface disposed about shockwave generating portion defines the type of shockwave generated.

Optionally the shockwave focal surface may be configured to produce at least one or more shockwaves for example including but not limited to the group consisting of focused shockwave, short focused shockwave, long focused shockwave, unfocused shockwaves, linear unfocused shockwaves, radial unfocused shockwaves, the like or any combination thereof.

Optionally if the pressurized fluid source is compressed air, most preferably the high pressure regulator may deliver a fluid pressure of up to about 100 bar to the shockwave applicator from the high pressure fluid source.

Optionally if the pressurized fluid source is compressed air, optionally and preferably the high pressure regulator may deliver fluid pressure of about 70 bar to the shockwave applicator from the high pressure fluid source.

Optionally if the pressurized fluid source is Carbon dioxide ($CO_2$), optionally and preferably the high pressure regulator may deliver a fluid pressure of about 60 bar to the shockwave applicator from the high pressure fluid source.

Optionally if the pressurized fluid source is Carbon dioxide ($CO_2$), then preferably the high pressure regulator may deliver a fluid pressure of about 56 bar to the shockwave applicator from the high pressure fluid source.

Optionally and preferably the projectile may be reloaded with a solenoid reloading apparatus, most preferably provided for placing the projectile at the start position prior to subsequent shockwaves generation.

Optionally the applicator may comprise an internal pressure reservoir chamber.

Optionally the system according to the present invention may further comprise an electronics module comprising a communication module to communicate with at least one or more auxiliary device. An auxiliary device may for example include but is not limited to at least one or more members selected from the group comprising an imaging device, ultrasound, X-ray, MRI, functional MRI (fMRI), CT, computer, server, smartphone, mobile telephone, portable device comprising processing and communication capabilities, healthcare provider computerized system, medical device console, the like or any combination thereof.

An optional embodiment of the present invention provides a high pressure ballistic shockwave applicator for producing extracorporeal shockwaves, the device may comprise a projectile accelerating portion including a projectile within an accelerating conduit; the accelerating conduit having a proximal end and a distal end; wherein the accelerating portion may be securely associated with a shockwave generating portion and/or treatment head disposed about the distal end; and wherein the projectile is accelerated from the proximal end to the distal end; the shockwave generating portion is provided in the form of a shockwave treatment head including a shockwave generating surface disposed about a proximal end of the shockwave generating portion and the distal end of the accelerating conduit, wherein the projectile is accelerated toward and collides with the shockwave generating surface to generate the shockwave; characterized in that the accelerating portion is configured to accelerate the projectile utilizing an operational pressure from about 50 bar up to about 100 bar for generating a ballistic shockwave.

Optionally the high pressure ballistic shockwave applicator may further comprise a solenoid reloading apparatus provided to reload the projectile at the proximal end of the accelerating conduit.

Optionally the shockwave generating surface may be configured to generate focused or unfocused shockwave, or any combination thereof.

An optional embodiment of the present invention provides a method for extracorporeal shockwave treatment with a ballistic shockwave system according to optional embodiments of the present invention, the method comprising: identifying and sizing a target treatment area for extracorporeal shockwave treatment with an imaging device; identifying at least one or more treatment protocol parameters relative to the targeted treatment area, the parameters selected from the group consisting of shockwave focal zone, shockwave intensity, shockwave frequency, number of shockwaves, depth of treatment, size of treatment area or any combination thereof; Setting the extracorporeal ballistic shockwave system to generate shockwave according to the treatment protocol parameters; and generating a ballistic shockwave according to the treatment settings, characterized in that the ballistic shockwave system utilizes an operational pressure of at least 50 bar to generate the ballistic shockwave.

Optionally the treatment protocol may be adapted to provide non-invasive extracorporeal lithotripsy treatment wherein the target within a treatment area is a calculus, for example including but not limited to a kidney stone, gallstone or the like.

An optional embodiment of the present invention provides a method for extracorporeal shockwave treatment with a ballistic shockwave system having a plurality of treatment heads, the method comprising: identifying and sizing a target within a treatment area for extracorporeal shockwave treatment with an imaging device; Identifying at least one or more treatment protocol parameters relative to the targeted treatment area, the parameters selected from the group consisting of shockwave focal zone, shockwave intensity, shockwave frequency, number of shockwaves, depth of treatment, size of treatment area or any combination thereof; wherein the treatment protocol parameters are configured both for each treatment head of the plurality of treatment heads and collectively for the system; Setting the extracorporeal ballistic shockwave system to generate shockwave according to the treatment protocol parameters; wherein the settings are configured for each treatment head to produce the required a systemic and/or collective shockwave treatment effect; Generating ballistic shockwave according to the treatment settings, with the plurality of treatment heads characterized in that the ballistic shockwave system utilizes an operational pressure of at least 50 bar to generate the ballistic shockwave.

Optionally the treatment protocol may be adapted for non-invasive extracorporeal lithotripsy and wherein the target treatment area is a calculus.

Optionally the individual treatment heads of the plurality of treatment heads are utilized to create individual treatment focal zone about the target treatment area. Optionally the individual treatment focal zones may be collectively configured to produce the systemic shockwave treatment effect.

Within the context of this application the term "Shock wave" or "shockwave" is intended to mean a large-amplitude compression wave, produced by an explosion or by supersonic motion of a body in a medium.

Within the context of this application the term "Treatment zone" is intended to mean the area on the human or animal tissue where, upon the application of the shock wave to the skin of said human or animal, the pressure is higher than about −6 db (50%) from maximum pressure peak according to standard IEC 61846.

Within the context of this application the term "Ballistic technology" is intended to mean a technology which based on flight dynamics of projectiles, either through the interaction of the forces of propulsion, the aerodynamics of the projectile, atmospheric resistance, and gravity.

Within the context of this application the term "Solenoid" is intended to mean a coil wound into a tightly packed helix.

Within the context of this application the term "Electro hydraulic" is intended to mean—a technology involving or produced by the action of very brief but powerful pulse discharges of electricity under a liquid resulting in the generation of shock waves.

Within the context of this application the term "Piezoelectric" is intended to mean Generation of stress in such crystals subjected to an applied voltage.

Within the context of this application the term "bar" is intended to mean unit of pressure, that may interchangeably be identified according to SI units for pressure namely Pascal and/or any equivalent unit for example including but not limited to atmospheres, psi, torr, or the like, according to the conversion chart as is known in the art wherein, 1 bar=0.98692 Atm (atmosphere)=0.1 Mpa (Mega pascal) =100000 Newton/square meter=14.5038 psi.

Within the context of this application the term "Impact" is intended to mean the force or impetus transmitted by a collision of projectile with the tip, focusing of impact converted to shock wave and/or pressure waves and/or impact waves and/or mechanic waves and/or acoustic waves, the like and/or any combination thereof.

Within the context of this application the term "impact zone" or treatment zone are intended to mean the place where the shock wave is applied on the body of the human or animal.

Within the context of this application the terms "direct coupling" is intended to mean that the treatment head and/or tip touches impact zone directly.

Within the context of this application the term "liquid coupling" is intended to mean that a liquid buffer separates between the tip and the impact zone.

Within the context of this application the term "focal size" is intended to mean impact or force focused on limited area.

Within the context of this application the terms "applicator" or "shock wave applicator" are intended to mean a carrier unit for shock wave comprising pipe, valve, projectile and tip.

Within the context of this application the term "gas" or "flowing fluid" and/or "fluid pressure" is intended to mean air or carbon-dioxide ($CO_2$), nitrogen or other gases and/or flowing fluids that may be compressed under pressure.

Within the context of this application the term "internal gas cylinder" is intended to mean a cylinder with small capacity of gas, integrated with applicator, wherein the cylinder may be integrated or otherwise associated with the applicator according to premedical device of the present invention.

Within the context of this application the term "external gas cylinder" is intended to mean an energy source, and/or a cylinder with large capacity of gas within the cylinder wherein the cylinder may be connected and/or otherwise associated with the medical device of the present invention by high gas pressure tubes.

Within the context of this application the term "air pressure pump" or "pneumatic piston" is intended to mean energy (air) filling source, electrohydraulic or other pressure pump for pressure supporting.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Importantly, this Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A-C are schematic diagrams of an optional high pressure ballistic shockwave device and/or applicator, utilized for generating and applying extracorporeal shockwave therapy, according to optional embodiments of the present invention;

FIG. 9A-B show a schematic illustration of a high ballistic shockwave system according to optional embodiments of the present invention.

DESCRIPTION OF THE PREFERRED EMBODIMENTS

The principles and operation of the present invention may be better understood with reference to the drawings and the accompanying description. The following figure reference labels are used throughout the description to refer to similarly functioning components are used throughout the specification hereinbelow:

50 Treatment area;
52 treatment target;
60 Auxiliary device;
100, 101 High Pressure Ballistic ESWT system;
105 Shockwave;
105L unfocused linear shockwave;
105F focused shockwave;
105R unfocused radial shockwave;
110 High Pressure source;
112 External pressure source;
114 Reservoir pressure source;
120 flow control module;
122 pressure regulator;
124 valve;
126 trigger
130 ESWT applicator;
132 applicator projectile reload apparatus;
134 recoil pressure accumulator reload apparatus;
138 solenoid reload apparatus
140 Ballistic projectile accelerating apparatus;
140$d$ distal portion;
140$p$ proximal portion;
142 projectile and/or striker;
144 internal conduit;
144$d$ conduit distal end;
144$p$ conduit proximal end;
145 pressure seal and/or O-ring;
146 inlet;
147 pressure relief opening;
148 stabilizer;
150 Shockwave generator and/or treatment head;
152 shockwave generating surface;
153 coupling seal;
154 treatment head membrane;
155 treatment head coupling bracket;
156 treatment head medium;
158 shockwave focal surface;
160 electronics module;
162 power supply;
164 processor controller;
166 display;
168 communication module.

Figure 1A:
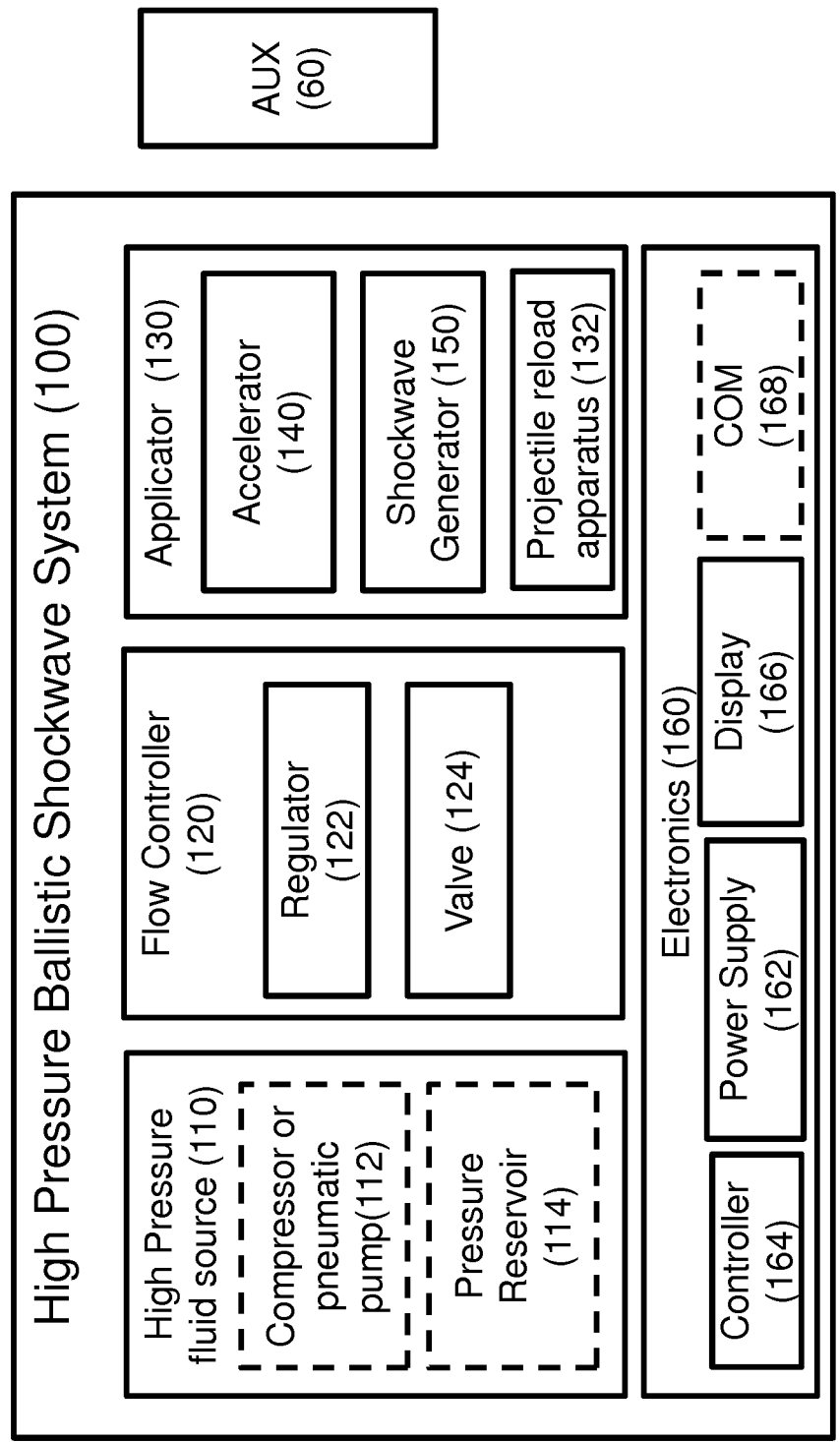
FIG. 1A-B are schematic block diagrams of optional systems for a high pressure ballistic shockwave system, most preferably utilized for extracorporeal shockwave therapy, according to optional embodiments of the present invention.
Figure 1B:
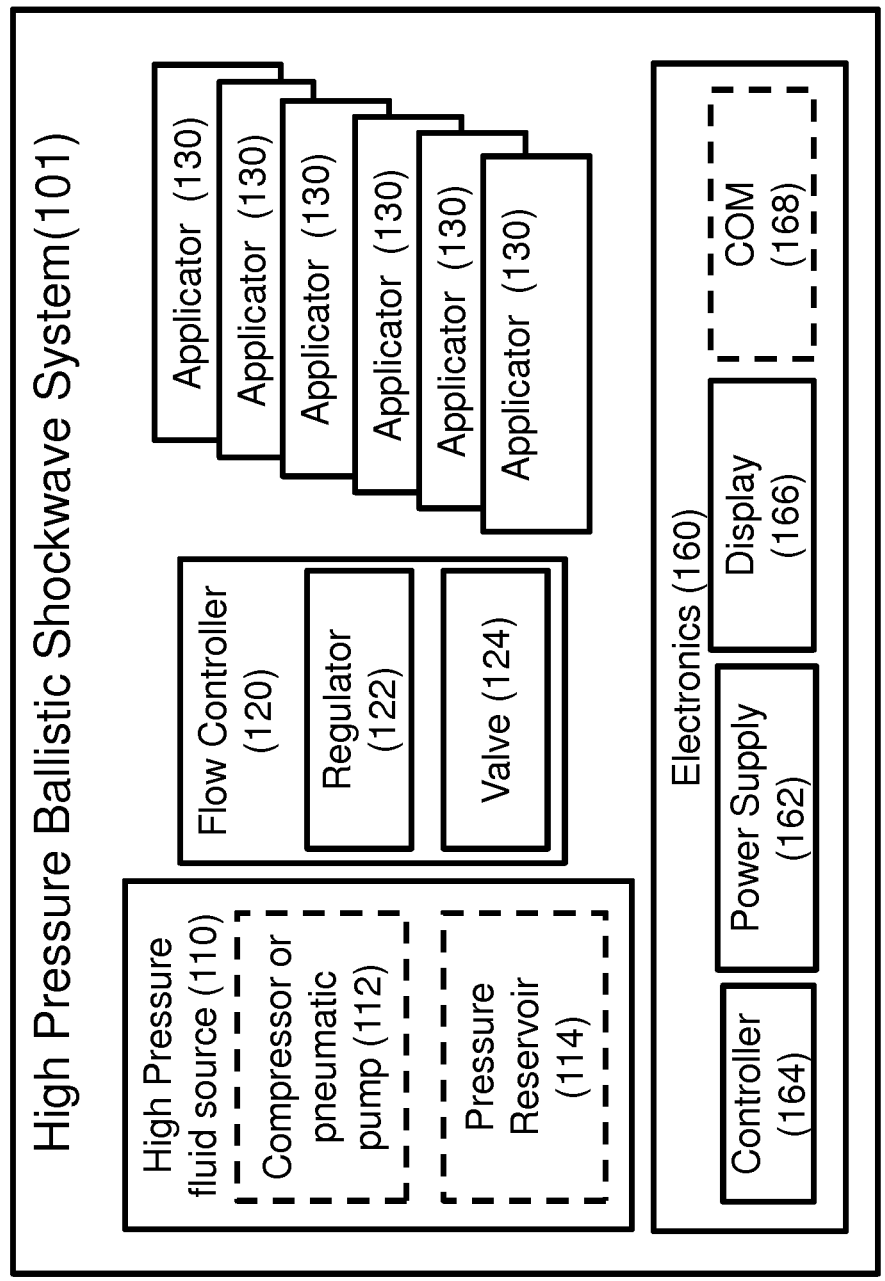

Referring now to the drawings, FIG. 1A-B are schematic block diagrams of an exemplary system according to the present invention for a high pressure extracorporeal ballistic shockwave treatment system 100, 101. As its name suggests a ballistic shockwave system 100, 101 generate shockwaves 105 as a result of a ballistic collision between a projectile 142 and a shockwave generating surface 152. Most preferably, projectile 142 may be accelerated and/or propelled toward surface 152 where most preferably projectile 142 collides into surface 152 producing a shockwave 105. Most preferably projectile 142 is energized and/or accelerated and/or propelled by utilizing optional high pressure fluid sources 110. Optionally and preferably projectile 142 is accelerated within conduit 144 to obtain a velocity from about 40 m/s up to about 180 m/s (meters per second).

Optionally the energy provided by the energized projectile 142 with system 100 provides for generating a shockwave pressure of about 300 bar or more, optionally a shockwave pressure from about 50 bar and up to about 350 bar, preferably from about 200 bar up to about 300 bar.

Optionally the energized projectile 142 may provide for generating a shockwave intensity equivalent to about up to about 80 Joules (J), optionally about 75 J, about 50 J, optionally and preferably from about 20 J and up to about 60 J, or the like.

Most preferably system 100, 101 is characterized in that it provides for producing extracorporeal ballistic shockwave utilizing a high pressure source of up to about 300 bar, while optionally and most preferably the operational pressure is up to about 100 bar, more preferably 70 bar when the pressurized fluid medium is air, and preferably about 56 bar when the pressurized fluid medium is carbon dioxide.

FIG. 1A shows an optional embodiment of ballistic ESWT system 100, comprising a high pressure fluid source 110, at least one or more fluid flow controller 120 and applicator 130.

Most preferably high pressure fluid source 110 provides for powering and/or energizing projectile 142. Most preferably a high pressure fluid source, for example provided in the form of high pressure gas cylinder, may be provided with a pressure of up to about 300 bar.

Most preferably projectile 142 may be provided from tempered steel.

Optionally projectile 142 weight and dimensions may be configured according to the system 100 or any portions thereof or associated requirements, and/or treatment requirements and/or parameters. Optionally projectile parameters for example weight and size may be configured relative to and/or as a function of size and weight of treatment head 150 or portions thereof for example including but not limited to surfaces 152, 158.

Optionally projectile 142 may weigh up to about 30 g (grams), optionally from about 5 g up to about 30 g, optionally up to about 20 g, optionally and preferably about 10 g, and optionally more preferably from about 6 g to about 8 g.

Optionally the dimensions of the projectile may for example be from about 10 mm up to about 30 mm, more preferably from about 15 mm up to about 20 mm.

Optionally high pressure source 110 may be provided in a plurality of optional forms for example including but not limited to at least one or more of an internal gas cylinder, an external gas cylinder, gas pressure pump, gas pressure reservoir 114, compressor 112, pneumatic pump 112, the like, or any combination thereof.

Optionally and most preferably high pressure source 110 may be provided in the form of gaseous flowing fluid, for example including but not limited to nitrogen, carbon dioxide or compressed air, or the like.

Optionally and most preferably high pressure source 110 may be provided as a direct pressure source and/or an indirect pressure source.

An optional embodiment of the present invention provides for utilizing pressure source 110 as a direct pressure source, that may for example be realized in the form of a portable high pressure gas cylinder and/or balloon.

An optional embodiment of the present invention provides for an indirect source of high pressure flowing fluid. For example an indirect pressure source may be realized by way of utilizing a combination of an external high pressure gas cylinder (external gas cylinder) that is coupled with a gas pressure reservoir (internal gas cylinder) most preferably such an indirect high pressure source is mediated by a flow controller 120 for example a controlling valve 122 and/or pressure regulator 124 to control the release of high pressure, most preferably in the form of operational pressure, from an external source high pressure source 110, providing 300 bar, to pressure reservoir 114, maintaining operational pressure from about 50 bar to about 100 bar. Optionally and most preferably pressure reservoir 114 may be utilized only as necessary for the generation of a shockwave 105.

Most preferably system 100 comprises at least one or more flow controller 120. Optionally and preferably flow controller 120 may be provided in a plurality of optional forms for example including but not limited to a valve 124, solenoid valve, pressure regulator 122, pneumatic piston, pneumatic valve, the like, or any combination thereof provided for controlling the flow of high pressure fluid source 110 within any portion of system 100.

Optionally and preferably flow controller 120 may comprise mechanical flow control members for example including but not limited to a trigger, valve gating member, valve open and close apparatus, or the like mechanical flow control member to control and/or harness the high pressure fluid source 110.

Optionally flow controller 120 may be provided in the form of an electronic processor having control of a valve 124, pressure regulator 122 or the like device.

Optionally system 100 may comprise a plurality of flow controllers 120 disposed within system 100 to control high pressure fluid flow between at least two members or portions thereof, for example including but not limited to a first pressure source to a second pressure reservoir, a pressure source to at least one or more applicator, the like or any combination thereof.

Optionally flow controller 120 provides for regulating pressure differentials between a pressure source 110 for example comprising high pressure of up to about 300 bar to a pressure sink, for example including but not limited to applicator 130, therein most preferably providing for controlling the operational pressure of system 100, for example up to about 100 bar.

For example a high pressure source 110, for example in the form of gas cylinder 114 having a pressure of 300 bar, may utilizes optional flow controllers 120 to provide an applicator 130 with an operational pressure of about 60 bar and more preferably 56 bar when the fluid pressure source is carbon dioxide or an operational pressure of about 70 bar when the fluid pressure source is compressed air.

Optionally system 100 may comprise an optional electronics module 160. Optionally and preferably electronics module 160 comprises power supply 162, controller and/or processor 164 and display 166. Optionally electronics module 160 may further comprise a communication module 168.

Optionally controller and/or processor 164 may provide for controlling any portion of system 100. Optionally and most preferably controller 164 may provide for controlling flow controller 120 or any portion thereof, for example including but not limited to valves 124 and/or regular 122. Most preferably controller 164 may provide for controlling the treatment protocol utilized and provided by system 100. Optionally and preferably controller 164 may for example provide for controlling and/or setting applicator 130 parameters for example including but not limited to treatment focal zone, treatment frequency, shockwave parameters, shockwave amplitude, the like or any combination thereof.

Most preferably power supply 162 may be utilized to power system 100. Power supply 162 may for example be provided in the form for example including but not limited to photo-galvanic cells, battery, rechargeable battery, disposable batteries, capacitors, super capacitors, or a mains power supply line, the like power source or any combination thereof.

Optionally display 166 may be provided in optional forms for example including but not limited to indictors, alphanumeric display, touch screen, the like or any combination thereof.

Optionally communication module 168 may be provided for communicating with optional auxiliary devices 60 for example utilizing wireless communication protocols, cellular communication, wired communication, near field communication, the like and/or any combination thereof. Optionally auxiliary devices may be in communication with system 100 may for example include but is not limited to an imaging device, ultrasound, X-ray, MRI, functional MRI (fMRI), CT, computer, server, smartphone, mobile telephone, portable device comprising a processing and communication capabilities, healthcare provider computerized system, medical device console, other devices, the like or any combination thereof.

Most preferably applicator 130 provides for converting high pressure fluid from at least one or more high pressure fluid source 110, that is most preferably regulated and/or controlled with optional flow controllers 120, into shockwaves produced and delivered by applicator 130. Optionally applicator 130 may comprise at least two portions, an accelerator portion 140 and a shockwave generator portion 150.

Most preferably accelerator portion 140 provides a conduit 144 for energizing and/or accelerating a projectile 142 toward a target, most preferably a shockwave generating surface 152, provided to generate shockwaves. Most preferably accelerator portion 140 is configured to receive regulated and/or controlled high pressure flowing fluid, most preferably in the form of gas, from high pressure source 110, through fluid flow controller 120, where the delivered high pressure fluid is used to energize projectile 142 within conduit 144, toward shockwave generator portion 150.

Optionally and preferably shockwave generator portion 150 may for example be realized in the form extracorporeal shockwave treatment head comprising a shockwave generating surface 152.

Most preferably shockwave generator portion 150 and accelerating portion 140 are coupled or otherwise functionally and fluidly associated with one another to provide for shockwave generation.

Most preferably applicator 130 may further comprise a projectile reloading apparatus 132 that facilitates the formation of subsequent and/or successive shockwaves by reloading projectile 142 displacing it to its initial position within conduit 144 in preparation for a successive shockwave generation. Most preferably a flow regulator 122 for example in the form of a valve 124, solenoid valve or the like provides for reloading projectile within conduit 144 in an efficient and timely manner.

Optionally and preferably reloading apparatus 132 utilizes an optional fluid pressure source 110, for example pressure reservoir 114 and/or, with an optional flow controller 120 to displace projectile 142 to its initial position.

Optionally reload apparatus 132 may function by optional methods for example including but not limited to a pressure accumulator, harnessing recoil energy, electromagnetic power, air pressure, negative air pressure (vacuum), the like or any combination thereof.

Optionally, pressure accumulator provides for accumulating pressure released during projectile's displacement toward the distal end 140d of conduit 144 sufficient to propel projectile 142 back toward proximal end 140p.

Figure 8:
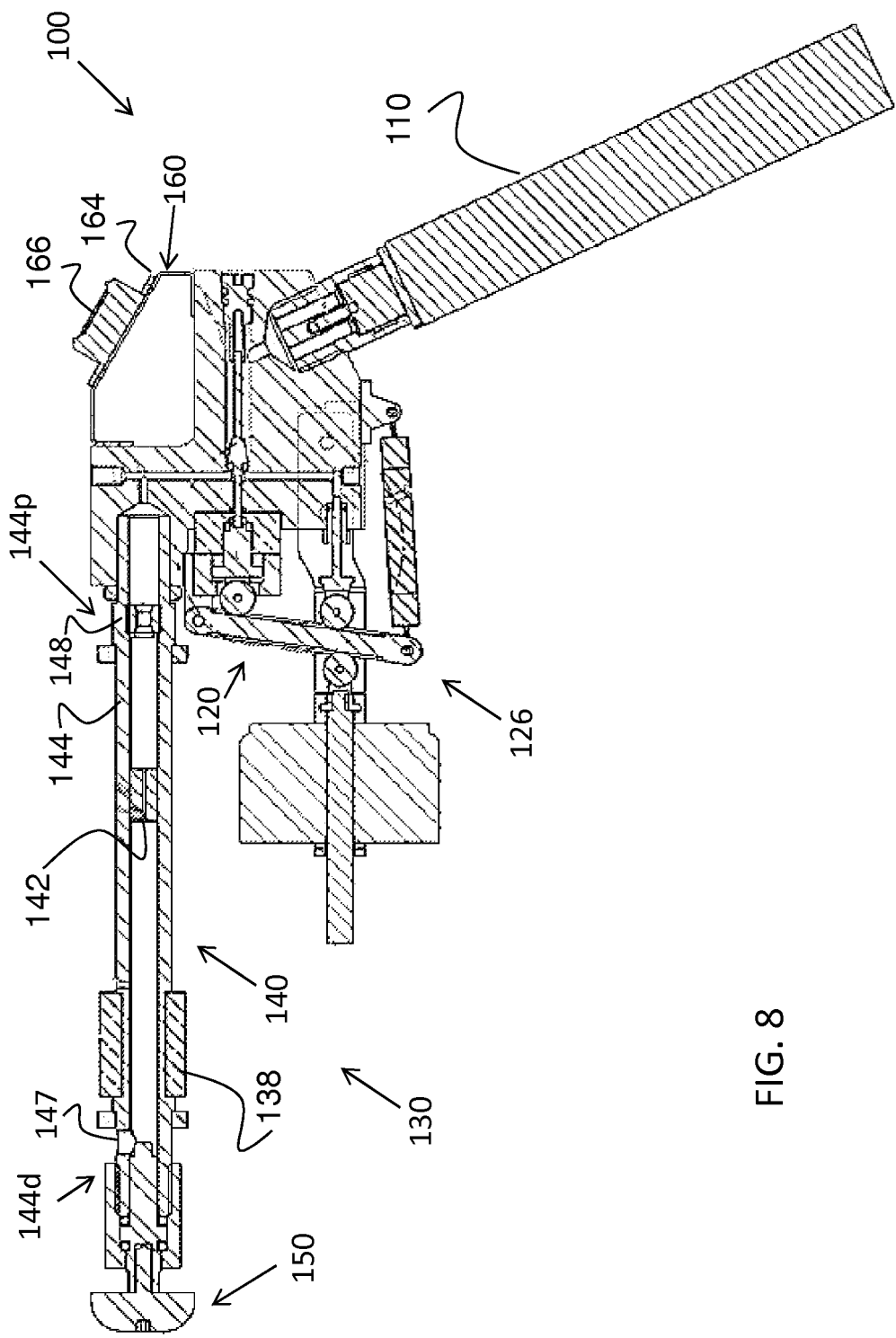
FIG. 8 shows schematic illustrations of a high ballistic shockwave system and applicator according to an optional embodiments of the present invention.

Optionally conduit 144 may comprise a pressure release opening 147, FIG. 8, disposed adjacent the distal end 140d optionally and preferably about shockwave generating surface 152. Most preferably pressure release opening 147 provides for release accumulated pressure built up within conduit 144.

Optionally recoil energy, may be utilized to reload projectile 142 onto the proximal end 140p, most preferably when the power generated is constant. For example, accumulated released pressure may be utilized as a form of recoil energy.

Optionally electromagnetic power may be utilized to generate an electromagnetic field to propel 142 back toward proximal end 140p.

Optionally a vacuum of 1-2 bar may be utilized to propel 142 back toward proximal end 140p.

FIG. 1B shows and optional system 101 comprising the components of system 100, as described in FIG. 1A, however with a plurality of applicators 130, for example as shown. Optionally system 101 may comprise any number of applicators 130 that may be arranged about treatment area to bring about a concerted delivery of shockwave to a particular region.

Optionally and preferably systems 100,101 indicate that a plurality of applicators 130 and/or flow controllers 120 and/or high pressure fluid source 110 may be arranged and or configured to bring about the required extracorporeal shockwave treatment at a target tissue.

Optionally system 100, 101 and any members thereof may be configured according to at least one or more treatment parameters for example including but not limited to size of treatment area, focal zone geometry, shape of treatment area, depth of shockwave penetration, shockwave parameters, shockwave characteristic, any combination thereof or the like. Optionally, shockwave parameters may for example include but are not limited to number of shockwaves, frequency of shockwaves and intensity of the shockwave, or the like.

Figure 2C:
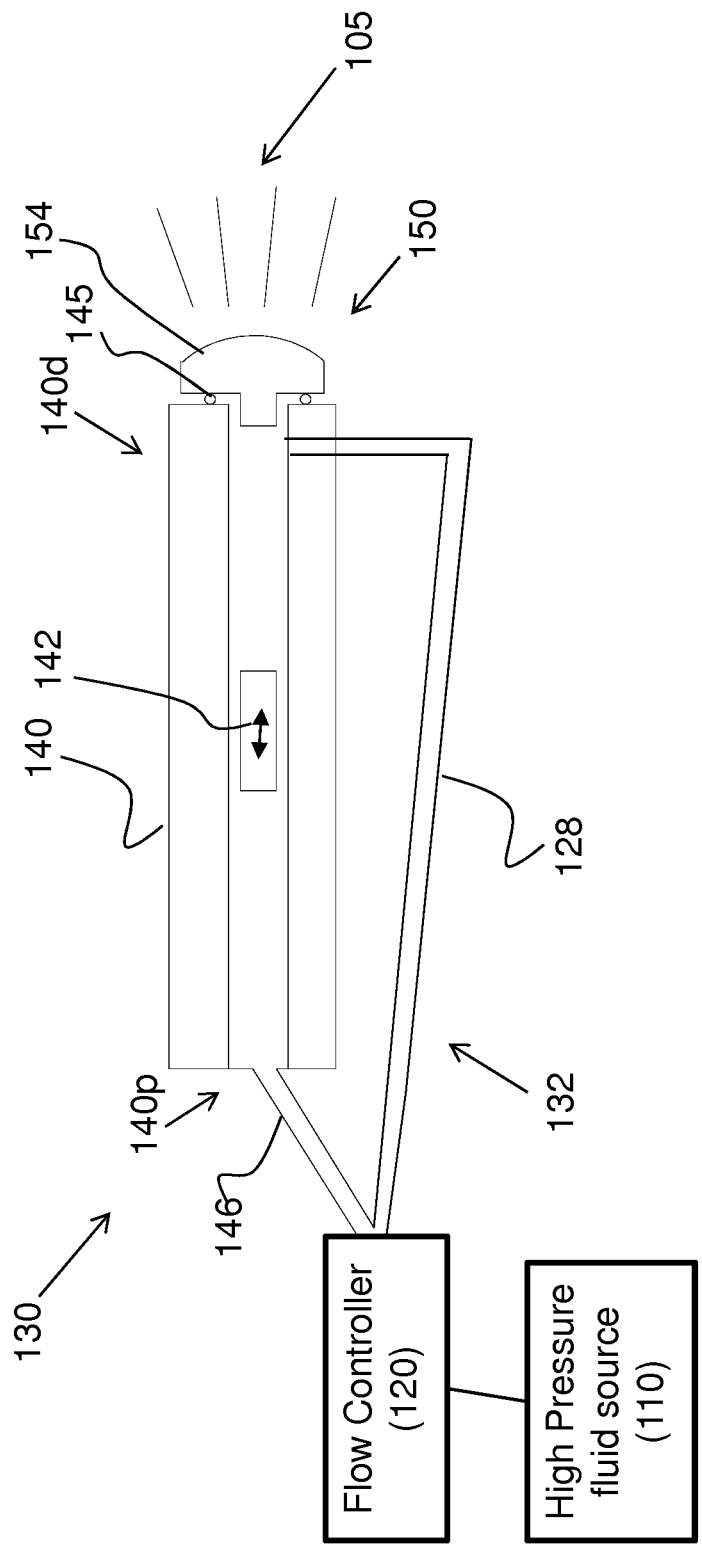

FIG. 2A-C show a schematic illustration of applicator 130 according to an optional embodiment of the present invention, in more detail. FIG. 2A depicts the applicator 130 prior to shockwave generation, while FIG. 2B depicts the applicator 130 during shockwave generation. FIG. 2A-B show applicator 130 comprising an accelerator portion 140 and a shockwave generator portion 150.

Most preferably accelerator portion 140 is coupled and securely fits with generator portion 150 about a seal 145, for example provided in the form of an O-ring or the like sealant. Most preferably portions 150 and 140 are functionally continuous and fluid with one another forming a controllably sealed conduit 144 that allows a projectile 142 to be propelled through the length of conduit 144 in an energy efficient manner.

Accelerating portion 140 most preferably provides for and facilitates energizing projectile 142 from a distal end 140d to a proximal end 144p. Most preferably portion 140 comprises a conduit 144 having a distal end 144d and a proximal end 144p. Most preferably conduit 144 comprises an inlet 146 disposed about its distal end 144d, provided for receiving operational pressure most preferably via flow control module 120 or directly from an optional fluid source 110. Most preferably the operational pressure received via inlet 146 is high pressure optionally from about 50 bar and up to about 100 bar. More preferably the operational pressure received through inlet 146 correlates with the type of compressed fluid utilized as a high pressure source 110. For example a carbon-dioxide based high pressure source 110 utilizes an operational pressure of about 60 bar and more preferably 56 bar. For example an air based high pressure source 110 utilizes an operational pressure of up to about 100 bar and more preferably about 70 bar.

Most preferably the operational pressure received through inlet 146 is controllable and may be controlled with at least one or more flow control members 120 for example including but not limited to a regulator 122, valve 124, a pneumatic valve, solenoid valve, electromagnetic valve, the like or any combination thereof.

Most preferably the lumen of conduit 144 comprises projectile 142, as shown, that may be energized with high pressure operational pressure from about 50 bar up to about 100 bar. Most preferably projectile 142 is sealed within conduit 144 to provide for accelerating it form proximal end 144p to distal end 144d.

Therein most preferably operational pressure enters accelerator 140 at inlet 146 about proximal end 144p, where the high pressure fluid from source 110 and flow controller 120, energizes projectile 142 and propels it toward distal end 144*d* where it collides with at least a portion of generating portion 150, most preferably about shockwave generating surface 152.

Most preferably shockwave generating portion 150 provides for generating and/or producing a shockwave 105 that emanates from generating portion 150, through a treatment head membrane 154. Optionally and preferably shockwave generating portion 150 may be realized as an ESWT treatment head, for example as shown, that may also be referred to as a tip, and/or treatment tip.

Most preferably generating portion 150 also referred to as a treatment head, preferably comprises a shockwave generating surface 152, a focal surface 158, a treatment head membrane 154 and a shockwave propagating medium 156. Optionally generating surface 152 and focal surface 158 may optionally be provided as a single unit more preferably generating surface 152 and focal surface 158 are provided from two corresponding members that may be securely affixed and/or coupled to one another forming. Optionally generating surface 152 is replaceable following continued use.

Most preferably focal surface 158 and generating surface 152 are provided from solid and/or durable materials for example including but not limited to metal, metallic-alloys, or the like. Optionally and preferably generating surface 152 may be provided from tempered steel or the like metal and/or metallic alloy that withstands and is durable in a ballistic impact and collisions environment. Optionally and preferably focal surface 158 may be provided from stainless steel, or the like metal and/or alloys that is durable in and can withstands an aqueous environment.

Most preferably propagating medium 156 is disposed internally within and is sealed within portion 150 bound within membrane 154. Propagating medium 156 most preferably facilitates and provides for propagating the shockwave from the focal surface 158 and onto a treatment area and/or tissue through membrane 154. Most preferably propagating medium 156 may for example include but is not limited to a liquid, water, hydrogel, gel, the like or any combination thereof.

Most preferably a shockwave is generated when projectile 142 collides with shockwave generating surface 152. Most preferably the collision causes the kinetic energy of projectile 142 to transfer to surface 152 in the process converting the kinetic energy to shockwave 105, for example as schematically depicted in FIG. 2B. Most preferably following the collision between projectile 142 and surface 152, the shockwave propagates through medium 156 toward membrane 154, and then onto the targeted treatment area 50 (FIG. 9A-B).

Optionally and preferably membrane 154 may be provided from optional materials for example including but not limited to silicone, polyurethane, polymers, hybrid or the like materials, and/or biocompatible materials that may be placed in direct or indirect contact with a topical treatment area.

Optionally and preferably propagating medium 156 further provides a barrier that filters and/or minimizes the mechanical ballistic effect of the collision and its transition into a shockwave 105.

Most preferably the operational pressure received through inlet 146 is controllable and may be controlled with at least one or more flow control members 120 for example including but not limited to a regulator 122, valve 124, a pneumatic valve, solenoid valve, electromagnetic valve, the like or any combination thereof.

FIG. 2C shows a preferred and optional applicator 130 with a schematic illustration for a projectile reload apparatus 132. Most preferably reload apparatus 132 comprises a flow controller 120 to control the high pressure flow into conduit 128 utilized to reload projectile 142 from distal portion 140*d* to proximal portion 140*p* in preparation for a subsequent release of shockwave 105. Optionally reload apparatus 132 may utilize a plurality of dedicated flow controller 120, for example a first flow controller may be provided for inlet 146 controlling projectile 142 release toward distal end 140*d*, and a second flow controller 120 for controlling the projectile 142 return from distal end 140*d* toward proximal end 140*p*. Optionally and more preferably reload apparatus 132 may utilize a single flow controller 120 to control fluid flow through both inlet 146 and conduit 128.

Figure 3:
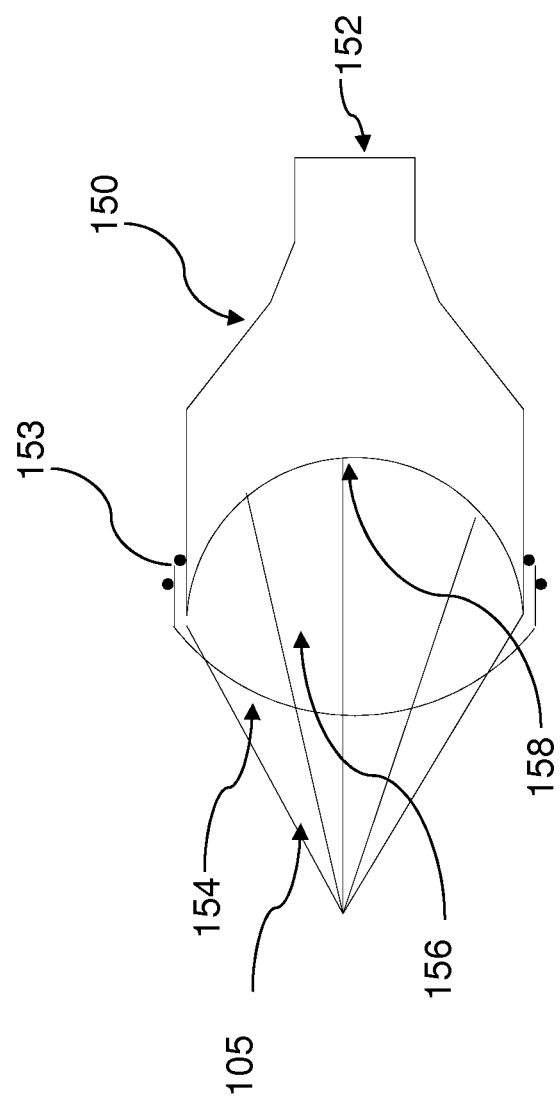
FIG. 3 is a schematic diagram of a ballistic extracorporeal shockwave treatment head, according to an optional embodiment of the present invention.

FIG. 3 shows a schematic illustrative cross-sectional view of an optional treatment head 150 according to an optional embodiment of the present invention. Treatment head 150 comprises a shockwave generating surface 152 provided for colliding with projectile 142 and generating the shockwave. FIG. 3 shows membrane 154 encasing a propagation medium 156 between membrane 154 and focal surface 158. Most preferably membrane 154 and focal surface 158 are coupled with a coupling seal 153 therein defining the opening and/or lumen for receiving propagation medium 156.

Optionally and preferably focal surface 158 provides for directing and/or focusing shockwave, where most preferably the shape assumed by surface 158 determines the characteristics of shockwave 105, focused or unfocused, provided by treatment head 150. FIG. 3 shows a focused shockwave 105 that emanates from treatment head 150 where the shockwave characteristics are most preferably determined by the geometry of shockwave focal surface 158. As shown, focal surface 158 is provided in the form of a concave surface, therefore most preferably leading to generating focused shockwaves, as depicted by leading lines of shockwave 105. Further examples are shown in FIG. 4A-E.

Optionally and preferably propagating medium 156 may for example be provided in liquid form for example including but not limited to water, gel, hydrogel or the like.

Optionally medium 156 provide for facilitating propagation of shockwave from focal surface 158 and onto treatment area and/or tissue through membrane 154. Optionally medium 156 and coupling seal 153 further act a barrier and/or momentum absorber for minimizing the effect of the mechanical movement and momentum of shockwave generating surface 152 and focal surface 158. Optionally, medium 156 provides a barrier for absorbing the mechanical movement of about 0.5 mm as a result of the ballistic collision between projectile 142 and surface 152

FIG. 4A-E show optional embodiments for optional configuration of treatment head 150. As show, the various shockwaves 105 emanating treatment head 150 may have different focal characteristics based on the focal surface 158 utilized for example including but not limited to shape, geometry, dimension, angle, curvature, the like or any combination thereof.

Figure 4:
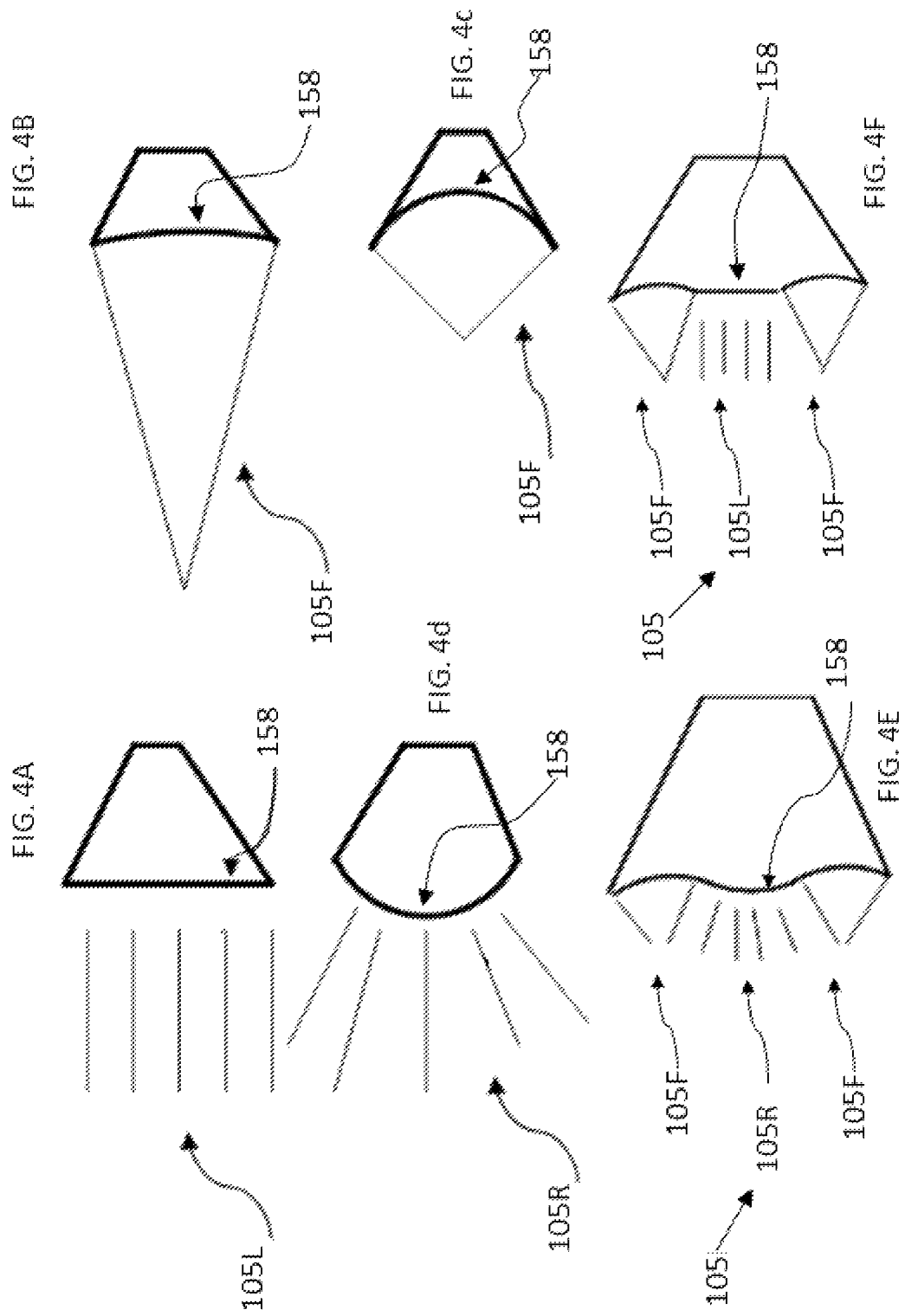
FIG. 4A-F show schematic illustrative diagrams of optional extracorporeal shockwave treatment heads according to optional embodiments of the present invention.

FIG. 4A shows an unfocused linear shockwave 105L that may be provided by a linear focal surface 158.

FIG. 4B-C shows a focused shockwaves 105F produced with a concave focal surface 158.

FIG. 4B shows a concave surface 158 leading to a focused shockwave 105F having a long focal length. Optionally and preferably the radius of the concave focal surface 158 configures the focal length of the resultant shockwave 105F.

FIG. 4C shows a further focused shockwave 105F produced with a concave focal surface 158, where the degree of curvature is higher than that shown in FIG. 4B, therein showing a shorter focal length, than that depicted in FIG. 4B.

FIG. 4D shows a treatment head 150 forming an unfocused radial shockwave 105R, due the convex shape and/or geometry of focal surface 158, wherein optionally and preferably the degree of dispersion depends on the radius of the surface 158.

FIG. 4E-F show optional embodiments of the present invention for a treatment head 150 comprising optional focal surface 158 having a mixed surface comprising various segments defining the shockwave 105.

FIG. 4E shows a mixed focal surface 158 comprising both convex at the edge and concave segments at its center, therein determining the shockwave configuration that lead to a shockwave front 105 comprising two focused shockwave 105F disposed at the edges and an unfocused radial shockwave portion 105R disposed in the center of the shockwave front 105.

Optionally and preferably this configuration of shockwave front 105, FIG. 4E, produces a shockwave front 105 having equal pressure at all points along its width, as the focused portions 105F at the edges make up for any energy and shockwave pressure losses that are normally experienced at the edges of different forms of unfocused shockwaves 105R.

FIG. 4F shows a mixed focal surface 158 comprising a linear segment about the middle section and a convex surfaces at its edges, therein determining the shockwave configuration that lead to a shockwave front 105 comprising two focused shockwave 105F disposed at the edges and an unfocused linear shockwave portion 105L disposed in the center of the shockwave front 105.

Optionally and preferably the shockwaves 105 depicted in FIG. 4F such configuration provide for increasing the energy at the edge of the shockwave front while flatting the energy bandwidth.

Figure 5:
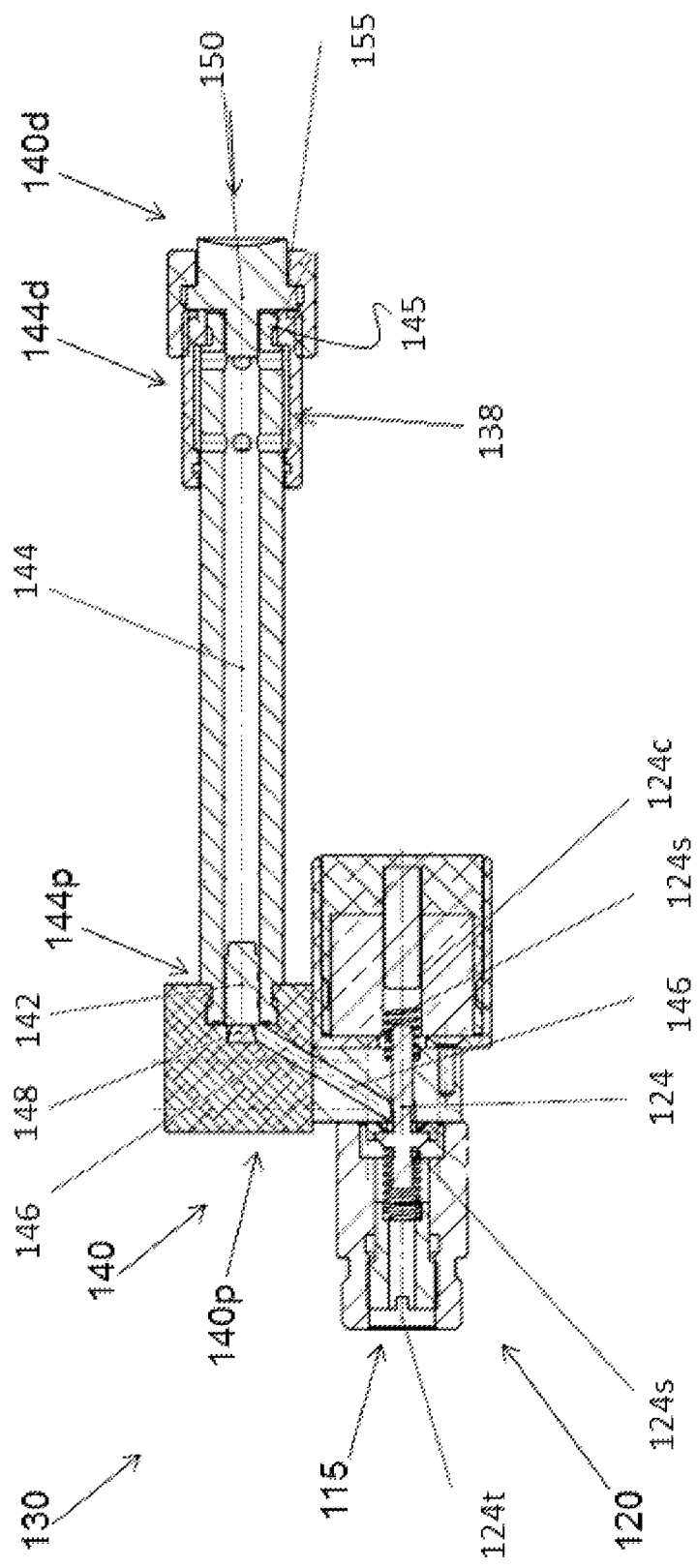
FIG. 5 shows a schematic illustration of a high ballistic shockwave applicator according to optional embodiments of the present invention.

Now referring to FIG. 5 showing an schematic illustration of an optional applicator 130 as previously described in FIG. 2A-B. Applicator 130 most preferably comprises shockwave generating portion 150, coupled with accelerating portion 140. Most preferably shockwave generating portion 150 is coupled with accelerating portion 140 about distal end 140*d*. Most preferably a coupling bracket 155 provides for mechanically coupling or otherwise associating portions 150 and 140. Most preferably seal 145 most preferably provided in the form of an O-ring provides for sealing portion 150 with portion 140, as previously described. As previously described generation portion 150 comprises a shockwave generating surface 152 provided for colliding with projectile 142 to generate and/or produce a shockwave 105. Most preferably shockwave focal surface 158 provides for determining the type of shockwave focused or non-focused, or a combination that will be propagate from shockwave 150.

Most preferably accelerating portion 140 comprises a conduit 144 having a distal end 140*d* and proximal end 140*p* as previously described. Most preferably projectile 142 is disposed within conduit 144 and may travel from proximal end 140*p* to distal end 140*d* to collide with surface 152 to generate a shockwave. Most preferably projectile 142 is propelled and/or energized by a high pressure fluid source 110 (not shown here) that may be controllably delivered via a fluid flow controller 120, to conduit 144 via inlet 146, as shown.

Most preferably conduit 144 comprises a projectile stabilizer 148, for example provided in the form of a magnet, electromagnet, or the like preferably for centering and/or stabilizing projectile 142 within conduit 144. Most preferably stabilizer 148 is disposed about the proximal end 140*p* adjacent to inlet 146.

Optionally and preferably distal end 140*d* of conduit 144 may be fit with a solenoid reload apparatus 138, provided to energize projectile 142 toward proximal end 140*p* in preparation for a successive shockwave. Optionally and preferably solenoid apparatus 138 may function concertedly with stabilizer 148 to propel projectile 142 toward proximal end 140*p*. Optionally and preferably solenoid reload apparatus 138 may be provided in the form of a solenoid and/or electromagnetic coil or the like.

Optionally and preferably solenoid apparatus 138 may utilize the momentum of projectile 142 as it travels through solenoid toward distal end 140*d* to generate a field that will propel projectile 142 toward stabilizer 148 at proximal end 140*p*. Most preferably the generated field is timed dependent and/or delayed such that it is activated and/or released only after projectile 142 collides with surface 152 to produces shockwave 105. Optionally solenoid apparatus 138 may provide for activating stabilizer 148 so as to create an electromagnetic field propelling projectile 142 toward proximal end 140*p*. Optionally and preferably solenoid apparatus 138 may be powered and/or controller and/or operated with electronics module 160 utilizing controller 164, Solenoid 138 return the projectile 142 to the start position, for example stabilizer 148, with a velocity of about 2 m/s to 4 m/sec.

Applicator 130 preferably comprises a flow control apparatus 120 comprise a valve 124, for example provided in the form of a gas pressure valve as shown. Most preferably valve 124 is a high pressure valve capable of handling high pressure of about 100 bar. Most preferably valve 124 is controlled with valve controller 124*c*. Most preferably valve 124 comprises a plurality of valve support springs 124*s* for facilitating valve controlling of its opening toward inlet 146. Most preferably valve 124 via controller 124*c* provides for controlling the fluid pressure entering and/or made available to inlet 146, therein controlling the pressure provided to accelerator 140 and conduit 144. Optionally and preferably valve 124 tension and the valve power required to open and/or closed valve 124 relative to inlet 146 may be controlled with a valve spring tension controller 124*t*. Most preferably tension controller 124*t* provides for adjusting valve 124 about springs 124*s* to control the power necessary to activate valve 124.

Most preferably flow control apparatus 120 is provided with high pressure supply from high pressure source 110 not shown through a coupling with high pressure inlet 115 allowing a compressed fluid at high pressure to flow from source 110 toward control apparatus 120 and eventually toward applicator 130 via inlet 146 to generate a shockwave by colliding projectile 142 with surface 152.

Figure 6:
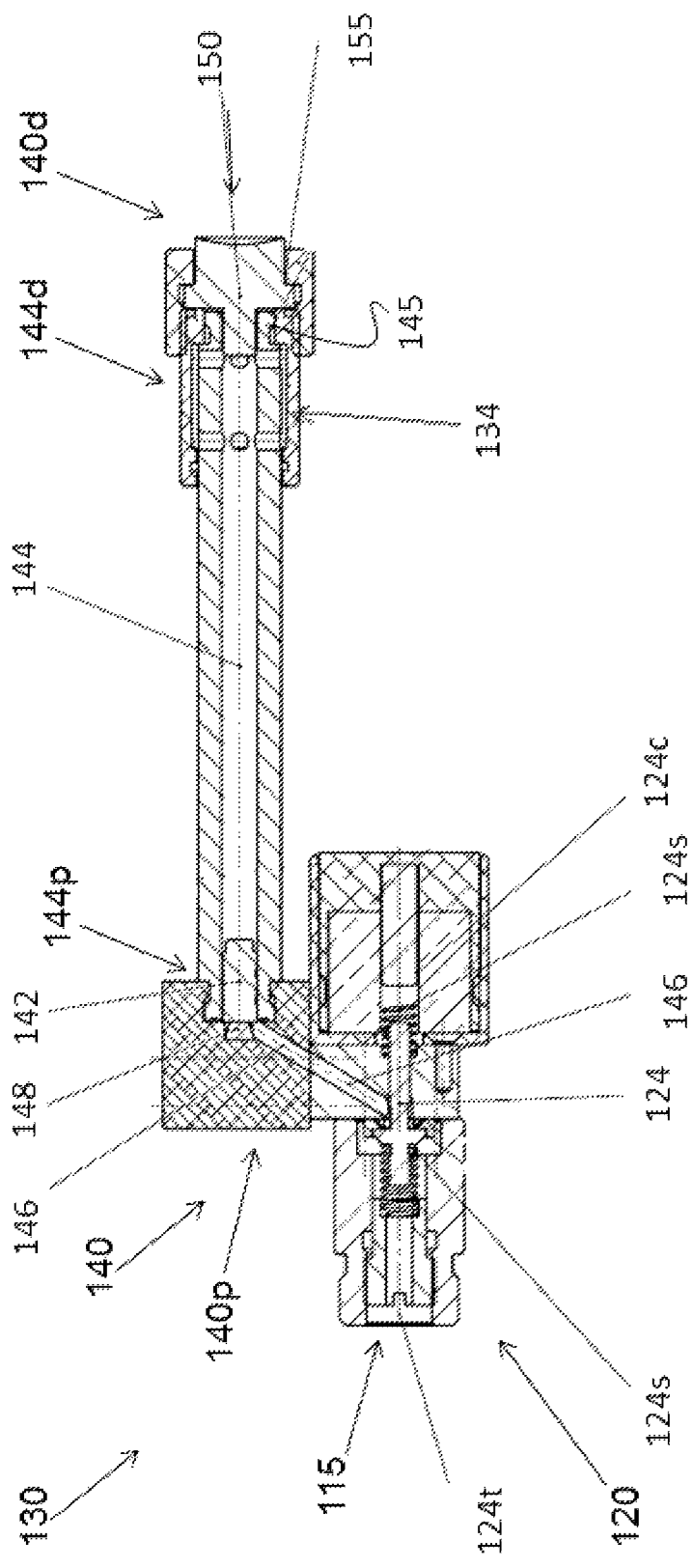
FIG. 6 shows a schematic illustration of a high ballistic shockwave applicator according to optional embodiments of the present invention.

FIG. 6 shows an optional embodiment of applicator 130 as that depicted in FIG. 5 however further comprising a reload apparatus 132 shown in the form of a recoil pressure accumulator 134. Most preferably pressure accumulator provides 134 for accumulating pressure released during projectile's displacement toward the distal end 140*d* of conduit 144 sufficient to propel projectile 142 back toward proximal end 140*p*.

Figure 7:
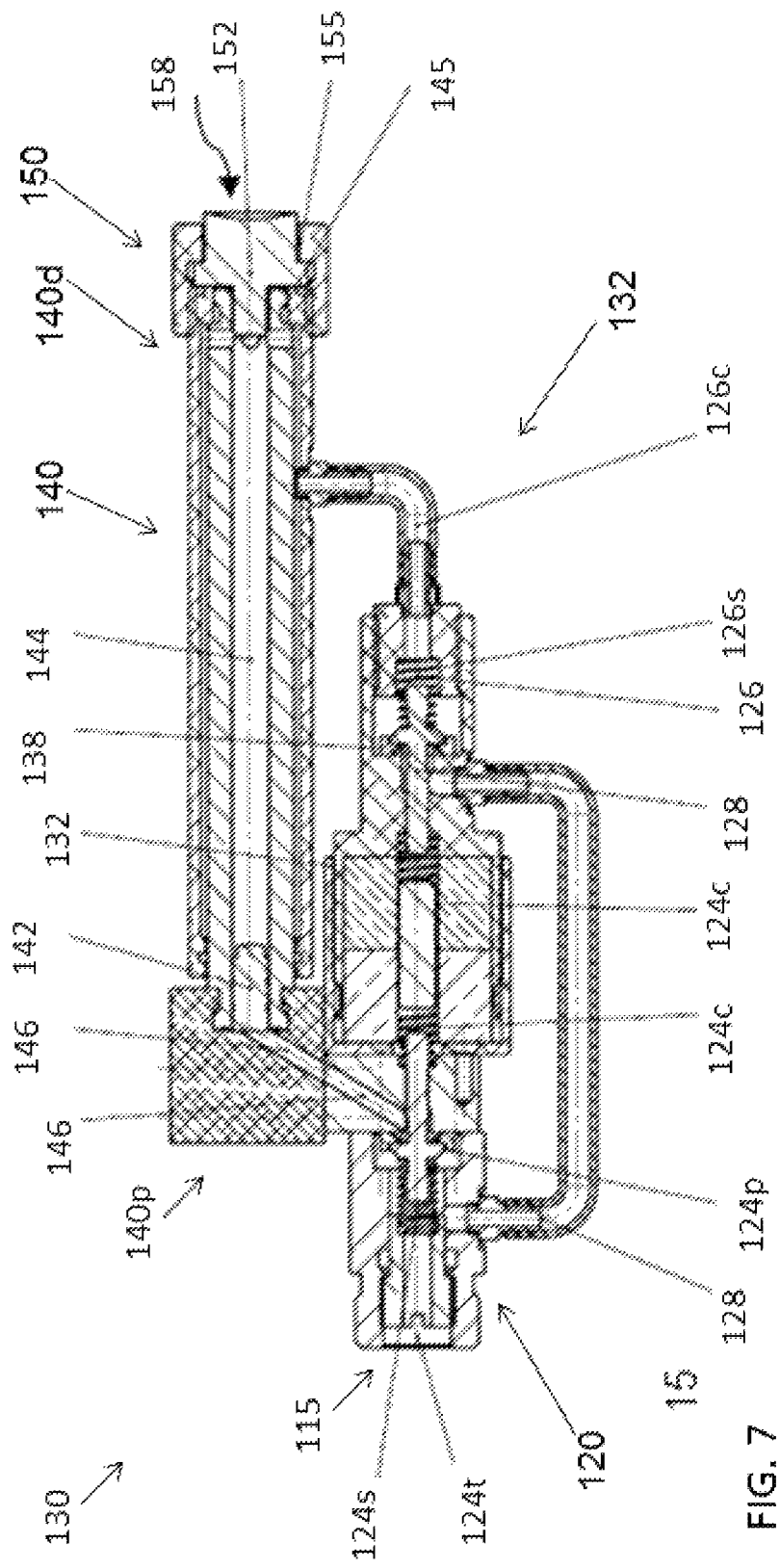
FIG. 7 shows a schematic illustration of a high ballistic shockwave applicator according to optional embodiments of the present invention.

FIG. 7 shows a further optional embodiment of applicator 130 similar to that depicted in FIGS. 5 and 6, however comprising a reload apparatus 132 utilizing a flow control apparatus 120, for example as shown in FIG. 2C. Most preferably control apparatus 120 is provided with a dual valve apparatus comprising a first valve 124 for controlling the high pressure flow to inlet 146 and a second valve 126 provided for controlling the reload function of apparatus 132. Most preferably valve 124 provides for controlling the forward motion of projectile 142 from proximal end 140p to distal end 140d generating a shockwave 105 by colliding with surface 152. Most preferably valve 126 provides for controlling the back motions of projectile 142 from distal end 140d to proximal end 140p. Most preferably second valve 126 provides for emerging projectile toward proximal end 140p optionally by way of releasing pressure adjacent to distal end 140dm, via conduit 126c. Optionally and preferably flow control apparatus 120 utilizes a single high pressure source 110 for both first valve 124 and second valve 126 via inlet 115 where high pressure is delivered to valve 124 directly and to valve 126 via a bypass conduit 128, therein both valves 124,1236 of flow controller 120 are provided with high pressure fluid from a single high pressure source 110.

FIG. 8 shows a further optional embodiment of the present invention for an extracorporeal ballistic shockwave treatment system 100 and in particular an ESWT applicator 130. FIG. 8 depicts an optional embodiment of system 100 comprising a high pressure fluid source 110 in the form of a gas cylinder comprising a compressed fluid, shown in the form carbon-dioxide. High pressure fluid source 110 is shown in the form of a portable gas cylinder comprising pressurized carbon-dioxide having a pressure of about 70 bar. Most preferably system 100 is configured to utilize an operational pressure of about 60 bar and more preferably at about 56 bar, at room temperature.

System 100 of FIG. 8 as shown comprises, electronics module 160 comprising a display 166 for displaying status of system 100, and controls 164 for controlling system 100. Optionally electronic module 160 may be utilized to communicate and/or otherwise link with an auxiliary device for example including but not limited to a mobile telephone, smartphone, computer, server, portable computer, medical device console, or the like device comprising processing and communication capabilities. Optionally an auxiliary device may provide for controlling and or communicating with system 100 via electronics module 160 or any member thereof.

FIG. 8 depicts applicator 130 comprising a reload apparatus 138 comprising a solenoid reload apparatus as previously described in FIG. 5, most preferably operated and/or controlled with electronic module 160.

Conduit 144 comprises a pressure release opening 147 disposed adjacent the distal end 140d at about generating surface 152. Most preferably pressure release opening 147 provides for release accumulated pressure built up within conduit 144.

Flow control 120, most preferably comprises a plurality of valves 124 and a triggering apparatus 126, for controlling the flow in applicator 130 from high pressure source 110. Most preferably flow control 120 provides for controlling the flow such that an applicator 130 is provided with an operational pressure of at least 56 bar and up to about 100 bar.

FIG. 9A shows a schematic illustration of an optional extracorporeal ballistic shockwave system 101, similar to that described in FIG. 1B. Most preferably system 101 depicts use of a ballistic extracorporeal shockwave in a lithotripsy application, wherein optionally a plurality of applicators 130 are utilized over a treatment area 50 comprising a treatment target 52 for example a calculus, kidney stone, gallstone, or the like.

System 101 comprises a plurality of ballistic shockwave applicator 130 according to optional embodiments of the present invention. Most preferably a plurality of applicators 130 utilized a high pressure source 110, as previously described, where the flow of the high pressure source may be controlled with flow controller 120 comprising at least one and optionally a plurality of regulators 122 and/or valves 124 in optional combinations.

Optionally system 101 may be in communication with an auxiliary device 60 for example to determine treatment parameters and/or protocol. Optionally treatment parameters may for example include but is not limited to shockwave amplitude, shockwave frequency, number of shockwaves, shockwave configuration, treatment location, focal zone determination, the like or any combination thereof.

Optionally and preferably use of a plurality of applicators 130, as shown, for example in a concerted manner, wherein all applicators have a single or joined target 52 as shown, may provide for dramatically reducing the number of shockwave required during treatment, for example lithotripsy. Optionally and preferably system 101 may provide for reducing the number of shockwaves required both due to the number of applicators 130 and in turn treatment heads 150 involved in the treatment. Optionally, the high energy and focal zone provided by the extracorporeal ballistic shockwave applicator 130 utilizing high operational pressure from about 50 bar to about 100 bar, according to the present invention, allows for reducing the number of shockwave required to perform the lithotripsy.

Optionally, system 101 utilizing a plurality of applicator 130 provides for collectively forming a collective focal zone from about 5 mm up to about 30 mm or more, about a target 52. Optionally each applicator 130 comprising system 101 may provide an individual focal zone 105F of variable size for example including but not limited to size selected from the group of up to about 5 mm, from about 0.5 mm up to about 4.5 mm, up to about 3 mm, up to about 2 mm, from about 1 mm to about 2 mm, up to about 1 mm or the like, where individual focal zone 105F may be directed toward target 52. FIG. 9B shows a schematic close up view of target 52, depicting individual focal zones 105F that provide for creating a systemic and/or unified focal zone and/or shockwave front 105 and/or systemic treatment effect about target 52. Optionally and preferably, having directed focal zones 105 and directing individual focal zones 105F, provides for increasing the energy provided to the lithotripsy target 52 therein greatly reducing the number of shockwaves, and/or treatments and/or time required to remove target 52.

Optionally the treatment parameters may for example include but is not limited to shockwave frequency, shockwave intensity, shockwave pressure, number of shockwave, depth of penetration, focal zone, target geometry, target size, target depth, the like, or any combination thereof.

The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A system for producing high pressure extracorporeal ballistic shockwaves, the system comprising:
    a. at least one high pressure ballistic shockwave applicator, comprising a projectile accelerating portion and at least one shockwave generating portion; said shockwave is generated by a collision between an accelerated projectile disposed within said projectile accelerating portion against a shockwave generating surface disposed in said shockwave generating portion;
    b. said shockwave generating portion comprising:
        i. said shockwave generating surface that is configured to withstand high pressure ballistic impact with said projectile;
        ii. a focal surface configured for shaping the generated shockwaves according to required treatment parameters;
        iii. a shockwave propagating medium provided for propagating the shockwave from the focal surface onto a treatment area through a membrane;
    c. a gaseous high pressure source and a high pressure flow controller to energize and accelerate said projectile in a controllable and directed manner; the system characterized in that said gaseous high pressure source is configured to provide an operational pressure from about 50 bar and up to about 100 bar, wherein said operational pressure is utilized to accelerate said projectile wherein said projectile generates a shockwave having an intensity from about 20 Joules up to about 80 Joules (J).

2. The system of claim 1 wherein said projectile is accelerated by said operational pressure to assume a velocity from about 40 m/s and up to about 180 m/s.

3. The system of claim 1 wherein said gaseous high pressure source has pressure from about 50 bar up to about 300 bar.

4. The system of claim 1 wherein said accelerating portion is further associated with a reloading apparatus selected from a pressure accumulator, solenoid based reloading apparatus, recoil energy harnesser, electromagnet, a magnet, or any combination thereof.

5. The system of claim 1 further comprising a projectile reload apparatus that utilizes said gas flow controller to reload projectile in preparation for a subsequent release of shockwave by way of controlling the high pressure flow through a bypass conduit.

6. The system of claim 4 wherein the reload apparatus comprises at least one flow controller configured for reloading the projectile by producing a negative pressure (essentially vacuum) utilized to pull said projectile toward proximal end.

7. The system of claim 5 wherein said reload apparatus comprises two flow control valves that are commonly connected to a single high pressure source wherein a first flow control valve is utilized for the forward movement of said projectile from the proximal end to the distal end for generating a shockwave; and wherein a second flow control valve is utilized for the reloading of said projectile from the distal end to the proximal end through a bypass conduit by way of releasing gas at high pressure adjacent to distal end to initiate the back-flow of said projectile.

8. The system of claim 1 wherein said shockwave applicator comprises a projectile stabilizer mounted around the accelerating conduit, said stabilizer selected from a magnet or electromagnet that is configured to create an electromagnetic field propelling the projectile toward proximal end.

9. The system of claim 1 wherein said shockwave generating portion is selected from a group of shockwave generating portions that comprise said shockwave focal surfaces that are configured to generate shockwave patterns selected from: focused shockwave, short focused shockwave, long focused shockwave, unfocused shockwaves, linear unfocused shockwaves or any combination thereof.

10. The system of claim 1 wherein the compressed gas providing said gaseous high pressure source is selected from the group consisting of:
    a. nitrogen or air wherein said high pressure regulator delivers an operational pressure from about 50 bar and up to about 100 bar to said shockwave applicator; or
    b. nitrogen or air wherein said high pressure regulator delivers an operational pressure of about 50-70 bar to said shockwave applicator; or
    c. carbon dioxide ($CO_2$), wherein said high pressure regulator delivers an operational pressure of about 60 bar to said shockwave applicator; or
    d. any combination thereof.

11. The system of claim 1 wherein said gaseous high pressure source is selected from the group consisting of:
    a. internal gas cylinder;
    b. external gas cylinder connected by a pipe;
    c. gas pressure reservoir;
    d. compressor;
    e. gas pressure pump;
    f. pneumatic pump;
    g. any combination thereof.

12. The system of claim 1 wherein said applicator comprises an internal pressure reservoir chamber that is configured to be filled from an external source.

13. The system of claim 1 wherein said propagating medium is selected from a group of materials that are characterized by low acoustic impedance, such as: water, hydrogel, gel, any combination thereof.

14. The system of claim 13 wherein said propagating medium further serves to deliver the shockwave energy from the shockwave generating portion while absorbing essentially all mechanical movement resulting from the ballistic collision between said projectile and said shockwave generating surface.

15. The system of claim 14 comprising a plurality of shockwave applicators that are arranged relative to one another about a treatment area to form a focal zone selected from:
    a. a collective focal zone;
    b. a unified focal zone;
    c. individual focal zones; and
    d. a shockwave front.

16. A high pressure ballistic shockwave applicator for producing extracorporeal shockwaves using a gaseous high pressure source controllable with a high pressure flow controller to energize and accelerate a projectile in a controllable and directed manner, the device comprising:
   a. a projectile accelerating portion including a projectile within an accelerating conduit; said accelerating conduit having a proximal end and a distal end; wherein said accelerating portion is connected with a shockwave generating portion about said distal end; and wherein said projectile is accelerated from said proximal end to said distal end; said projectile accelerating portion comprising a projectile stabilizer disposed around said proximal end said stabilizer selected from a magnet or electromagnet configured to create an electromagnetic field propelling the projectile toward proximal end; said accelerating conduit comprising an inlet at proximal end for receiving an operational pressure from about 50 bar up to about 100 bar from said high pressure source via said high pressure flow controller, said operational pressure utilized to allow said projectile to accelerate to a velocity of up to about 180 m/s so as to generate a ballistic shockwave when said projectile collides with a shockwave generating surface;
   b. said shockwave generating portion comprising said shockwave generating surface that is configured to withstand high pressure ballistic impact with said projectile; a focal surface configured for shaping the generated shockwaves according to required treatment parameters; a shockwave propagating medium provided for propagating the shockwave from the focal surface onto a treatment area through a membrane; wherein said shockwave generating surface is disposed about a proximal end of said shockwave generating portion at the distal end of said accelerating conduit, wherein said projectile is accelerated toward and collides with said shockwave generating surface to generate said shockwave.

17. The device of claim 16 further comprising a reload apparatus including at least one flow controller configured for reloading the projectile by producing negative pressure utilized to pull said projectile toward proximal end.

18. The device of claim 16 further comprising a bypass conduit associated with said flow controller to generate high pressure flow at distal portion to facilitate reloading projectile to proximal portion.

19. A method for extracorporeal shockwave treatment with a ballistic shockwave system utilizing a plurality of treatment applicators associated with treatment heads, the method comprising:
   a. identifying and sizing a target treatment area for extracorporeal shockwave treatment with an imaging device;
   b. identifying at least one or more treatment protocol parameters relative to said targeted treatment area selected from shockwave parameters and treatment parameters,
      i. wherein, the shockwave parameters are selected from the group consisting of shockwave focal zone, shockwave intensity, shockwave frequency, number of shockwaves; or any combination thereof and,
      ii. wherein the treatment parameters are selected from the group consisting of depth of treatment, size of treatment area, size of target, or any combination thereof;
      iii. said treatment protocol parameters are configured both for each of said plurality of treatment applicators and collectively for said system;
   c. setting said extracorporeal ballistic shockwave system to generate shockwave according to said treatment protocol parameters; wherein said setting are configured for each treatment applicator so as to produce the required a systemic shockwave treatment effect; and
   d. generating ballistic shockwave according to said setting, with said plurality of treatment heads characterized in that said ballistic shockwave system utilizes an operational pressure of at least 50 bar and up to about 300 bar to generate said ballistic shockwave.

20. The method of claim 19 wherein the treatment protocol is adapted for non-invasive extracorporeal lithotripsy and wherein the target treatment area is a calculus and wherein individual treatment applicators are utilized to create individual treatment focal zones about said target.

21. The method of claim 20 wherein said individual treatment focal zones are collectively configured to produce a systemic shockwave treatment effect.

* * * * *